United States Patent [19]

Sprunt et al.

[11] Patent Number: 4,631,964

[45] Date of Patent: * Dec. 30, 1986

[54] SHEAR ACOUSTIC ENERGY ANISOTROPY OF SUBSURFACE FORMATIONS

[75] Inventors: Eve S. Sprunt, Farmers Branch; Larry D. Smallwood, Duncanville, both of Tex.

[73] Assignee: Mobil Oil Corporation, New York, N.Y.

[*] Notice: The portion of the term of this patent subsequent to Dec. 30, 2003 has been disclaimed.

[21] Appl. No.: 715,795

[22] Filed: Mar. 25, 1985

[51] Int. Cl.$^4$ .............................................. G01N 29/00
[52] U.S. Cl. ...................................... 73/594; 73/571; 73/597; 73/599; 367/13
[58] Field of Search ................. 73/571, 594, 599, 618, 73/632, 597; 367/13

[56] References Cited

U.S. PATENT DOCUMENTS 3,537,541 11/1970 DeSai et al. ......................... 73/594
4,380,930 4/1983 Podhrasky et al. ................... 73/594

Primary Examiner—Howard A. Birmiel
Attorney, Agent, or Firm—Alexander J. McKillop; Michael G. Gilman; George W. Hager, Jr.

[57] ABSTRACT

Vertical shear acoustic energy anisotropy of a subterranean formation is measured from a core sample of such formation. The core sample is shaped by having its outer surface cut to provide a pair of flat or planar surfaces along parallel spaced-apart planes. A pair of planar shear transducers are placed in contact with the pair of planar outer surfaces, one of the transducers being a transmitting transducer and the other being a receiving transducer. Shear acoustic energy is transmitted through the core sample in a basically elliptical pattern having an azimuthal direction within a plane parallel to the planar outer surfaces of the core sample. Any differences in travel time, attenuation, waveform or other acoustic properties for the acoustic energy transmissions in a plurality of differing azimuthal directions are a measure of the shear acoustic energy anisotropy of the subsurface formation.

8 Claims, 3 Drawing Figures

SHEAR ACOUSTIC ENERGY ANISOTROPY OF SUBSURFACE FORMATIONS

BACKGROUND OF THE INVENTION

In sedimentary rocks, large vertical changes in properties occur as the result of changes in depositional conditions. Horizontal (or lateral) changes within a formation are known to occur, but these are generally much smaller. However, such changes may be of great importance in petroleum exploration and production. This variation of a property or properties with direction is termed "anisotropy". For example, horizontal anisotropy of elastic properties may affect the interpretation of seismic prospecting data. Petroleum production permeability anisotropy, caused by preferential arrangement of pores and/or fractures, is often an important factor in both primary and enhanced recovery. Stress anisotropy is important in petroleum well stimulation by hydraulic fracturing because the azimuth of induced fractures is generally parallel to the maximum horizontal stress direction. In many cases, the directions of natural and induced fractures are coincident.

SUMMARY OF THE INVENTION

The present invention is directed to a method for measuring acoustic energy anisotropy of a core sample taken from a subterranean formation and, more particularly, to a method for measuring changes in vertical shear acoustic velocity, attenuation, waveform or other acoustic properties which indicate the presence of lateral mechanical anisotropy in the sample due to fractures, stress, and other factors.

After the core sample is taken from a subterranean formation, it is shaped by having its outer surface cut or planed to provide a pair of flat or planar surfaces along parallel spaced-apart planes. A pair of planar shear transducers are placed in contact with said pair of planar outer surfaces, one of the transducers being a transmitting transducer and the other being a receiving transducer. Shear acoustic energy is transmitted through the core sample from the transmitting transducer to the receiving transducer in a basically elliptical, transmission pattern having an azimuthal direction within a plane parallel to the planar outer surfaces of the core sample. Thereafter, such shear acoustic energy is again transmitted through a plurality of differing azimuthal directions for the transmission pattern within such plane by the relative rotation of the core sample with respect to the pair of transducers. In one aspect, the pair of transducers are maintained in fixed position while the core sample is rotated. In an alternate aspect, the core sample is maintained in fixed position while the pair of transducers are simultaneously rotated. Any differences in travel time, attenuation, waveform or other acoustic properties of the plurality of acoustic energy transmissions in the differing azimuthal directions are measures of the shear acoustic energy anisotropy characteristic of the subterranean formation.

In a still further aspect, the core sample is shaped such that the pair of planar outer surfaces are perpendicular to the vertical orientation of the core sample within the subterranean formation. In this manner, the travel time, attenuation, and waveform differences of the shear acoustic energy are measures of the vertical shear acoustic energy anisotropy characteristic of the subterranean formation.

DESCRIPTION OF THE PREFERRED EMBODIMENT

Figure 1:
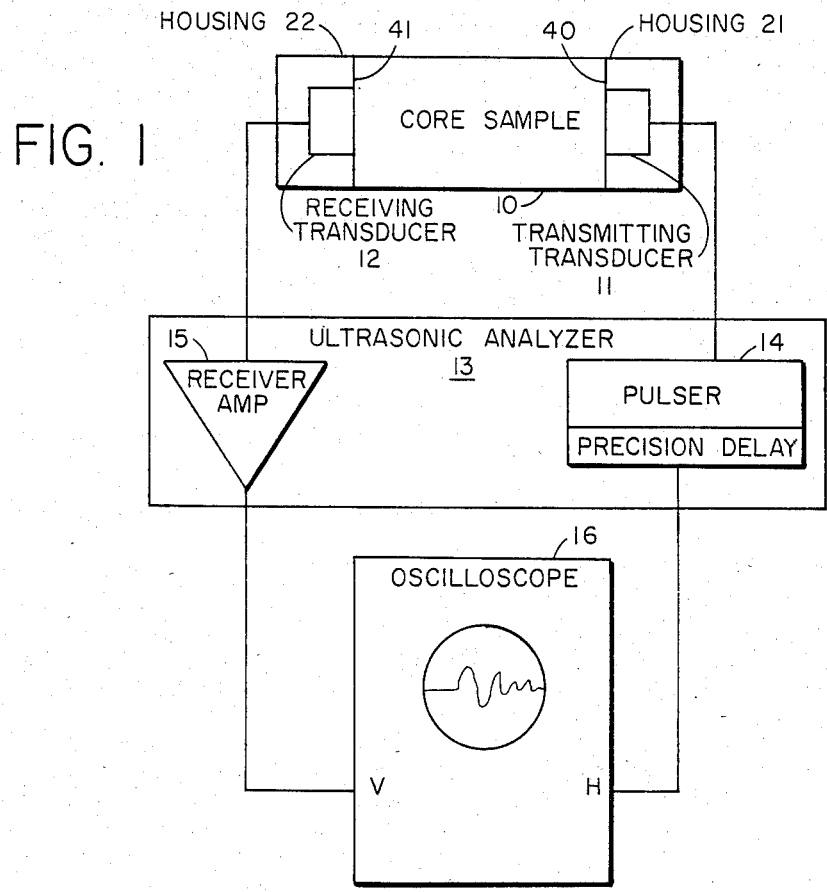
FIG. 1 illustrates a system for measuring acoustic velocity and recording waveforms of core samples from subterranean formations.

Referring now to FIG. 1, the core sample 10 from a subterranean formation to be examined in accordance with the present invention is mounted between a transmitting transducer 11 and its housing 21 and a receiving transducer 12 and its housing 22. These transducers are acoustic energy devices, such as piezoelectric or magnetostrictive crystals, designed to transmit and receive acoustic signals. Generation of the acoustic signal is carried out by the analyzer 13 including a pulser section 14 and a receiver section 15. The pulser section 14 produces an electrical pulse to excite the transmitting transducer 11, causing it to emit an ultrasonic pulse. This pulse travels through the material of core sample 10 and is converted by the receiving transducer 12 into an electrical signal which is applied to and conditioned by the receiver section 15 of the analyzer 13. This technique is called the "through transmission" technique as the pulse is transmitted by one transducer and received by another. An alternate embodiment might employ the "pulse-echo" technique whereby the pulse travels from the transducer through the material until it is reflected from an interface, such as the other end of the core sample. The reflected pulse may be received by the same transducer and converted into an electrical signal.

In either embodiment, the electrical signal, after being conditioned by the receiver section 15 of the analyzer 13, may be displayed on an oscilloscope 16 for visual interpretation and travel time calculation. The signal may also be recorded by other suitable devices, such as a Tektronix 7219AD model digital waveform recorder 17 or a strip chart recorder 19, for analysis.

The analyzer 13 may be a Panametrics, Inc. Model 5055PR, which combines a pulser/receiver in a single unit. The oscilloscope 16 may be a Hewlett-Packard 1743A model, which provides a dual time base with suitable time and amplitude expansion for an accurate selection of the acoustic time break.

Vertical shear acoustic travel time, attenuation, and waveforms through the core sample 10 are obtained by shaping the core sample to provide a pair of planar outer surfaces 40 and 41 along parallel spaced-apart planes through the core sample such that the perpendicular between such surfaces 40 and 41 corresponds to the vertical orientation of the core sample prior to being taken from the subterranean formation.

Figure 2:
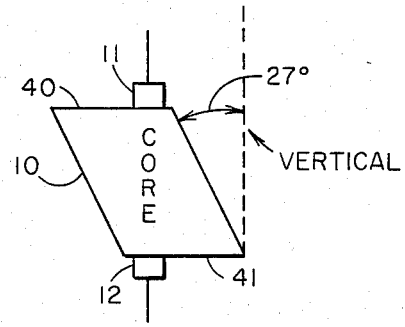
FIG. 2 illustrates a core sample taken from a deviated well and which is to be measured for shear acoustic properties by the system of FIG. 1.

The core sample does not have to be a right circular cylinder or a regular prism shape. Only the two surfaces 40 and 41 need to be planar and parallel. FIG. 2 illustrates how a core sample taken from a borehole deviated 27° from the vertical might be shaped.

Asymmetric shear wave energy is transmitted and received between the surfaces 40 and 41 of the core sample 10 by commercial, planar shear transducers 11 and 12, respectively, such as Panametrics Model V152. The transducers 11 and 12 are axially aligned and rotationally focused with respect to one another. Such asymmetric wave motion is detected by the receiving transducer to the exclusion of any other wave motion. The travel time, attenuation, and waveform of the shear wave through the core sample are representative of the shear acoustic energy transmission through the core sample.

To measure vertical shear acoustic energy anisotropy in accordance with the present invention, the shear acoustic energy is transmitted through the core sample in a plurality of differing transmission paths. Any change observed in the acoustic energy travel time, attenuation, waveform or other acoustic properties among such different transmission paths is an indication of vertical shear acoustic energy anisotropy. More particularly, the azimuthal directon of the asymmetric shear transmission pattern through the core sample is changed so as to effect the differing transmission paths.

Figure 3:
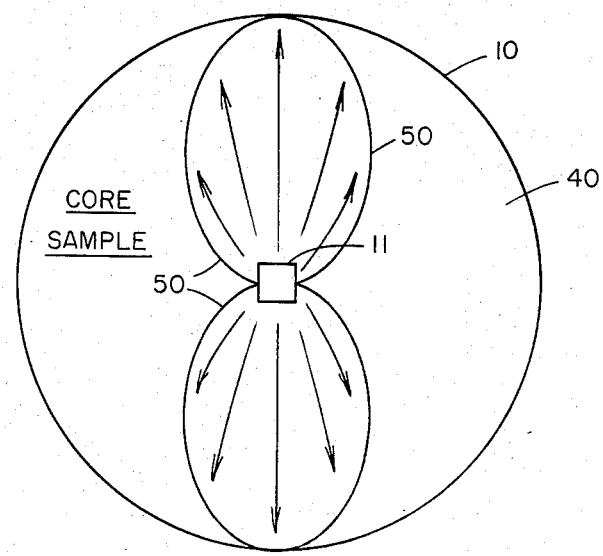
FIGS. 3 and 4 are top views of a core sample showing a pair of basically elliptical, shear wave acoustic energy transmission patterns through the core sample which are rotated 90° relative to one another in accordance with the method of the present invention.
Figure 4:
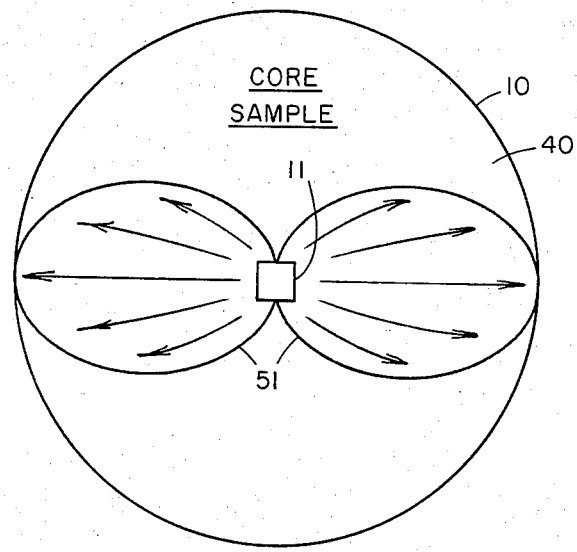

To achieve such an azimuthal direction change in the shear acoustic energy transmission pattern, the transducers 11 and 12 are simultaneously rotated so that the orientation of the asymmetrical shear energy moves in azimuthal direction with respect to the core sample about the perpendicular between the two outer planar surfaces of the core sample, such perpendicular corresponding to the vertical orientation of the core sample before being taken from the subterranean formation. During such rotation, the transducers continue to be positioned in the same locations on the outer surfaces 40 and 41. In the alternative, the core sample can be rotated while holding the transducers fixed in position. This may be further understood by referring to FIGS. 3 and 4 which are top views of the core sample showing the shear acoustic energy transmission through the core sample. Both FIGURES illustrate such transmission pattern as being basically elliptical in nature about the perpendicular between the two outer planar surfaces at the point of contact between the transmitting transducer and the core sample. In FIG. 4, the transmitting transducer and the core sample have been rotated 90° relative to one another such that the transmission paths 50 of FIG. 3 and 51 of FIG. 4 for the two shear acoustic energy transmissions differ by 90°.

In this manner, a plurality of shear acoustic energy transmissions can be completed having elliptical transmission patterns of differing azimuthal directions about the perpendicular through the core sample. As already noted above, any differences in travel time, attenuation, waveform or other acoustic properties of the shear acoustic energy transmissions for the differing azimuthal paths through the core sample are measures of a vertical shear acoustic energy anisotropy of the subterranean formation from which the core sample was taken.

In carrying out such measurements, the transducers 11 and 12 are held rigid and pressed against the outer surfaces 40 and 41 of the core sample. To ensure good contact, a simple press is utilized to provide a fixed pressure. One such press that has been successfully employed is described and illustrated in detail in U.S. Pat. No. 4,380,930 to Podhrasky and Sprunt, such U.S. patent being specifically incorporated herein by reference.

While the foregoing preferred embodiment of the invention has been described and illustrated, numerous modifications or alterations may be made without departing from the spirit and scope of the invention as set forth in the appended claims.

We claim:

1. A method for measuring shear acoustic energy anisotropy of a core sample taken from a subterranean formation, comprising the steps of:
   (a) shaping said core sample to provide a pair of planar outer surfaces along parallel spaced-apart planes,
   (b) transmitting shear acoustic energy into said core sample from a first of said planar outer surfaces, said acoustic energy traveling through said core sample to the second of said planar outer surfaces in a transmission pattern having a first azimuthal direction within a plane parallel to said planar outer surfaces,
   (c) receiving said acoustic energy at said second planar outer surface,
   (d) repeating steps (b) and (c) for a plurality of differing azimuthal directions for said acoustic energy transmission through said core sample, and
   (e) utilizing any differences in travel time, attenuation, waveform or other acoustic properties of said acoustic energy for said plurality of differing azimuthal directions of transmission patterns as a measure of the shear acoustic energy anisotropy characteristics of the subterranean formation from which said core sample was taken.

2. The method of claim 1 wherein said core sample is shaped such that said pair of planar outer surfaces are perpendicular to the vertical orientation of said core sample within said subterranean formation, whereby said differences in travel time, waveform, attenuation or other acoustic properties of said acoustic energy are measures of the vertical shear acoustic energy anisotropy characteristics of said subterranean formation.

3. The method of claim 1 wherein said shear acoustic energy transmission patterns are basically elliptical in nature about each of said differing azimuthal directions of transmission.

4. The method of claim 1 wherein said acoustic energy is transmitted and received by a pair of planar shear acoustic energy transducers in contact with said pair of planar outer surfaces of the core sample and the differing azimuthal directions of said acoustic energy transmission is provided by the relative rotation of said core sample with respect to said pair of transducers.

5. The method of claim 4 wherein said relative rotation is carried out by maintaining said pair of transducers fixed in position while said core sample is rotated.

6. The method of claim 4 wherein said relative rotation is carried out by simultaneously rotating said pair of transducers while said core sample is maintained in fixed position.

7. The method of claim 4 wherein said pair of transducers are axially aligned with respect to one another.

8. The method of claim 4 wherein said pair of transducers are rotationally focused with respect to one another.

* * * * *